United States Patent [19]

Glock et al.

[11] Patent Number: 5,350,734
[45] Date of Patent: Sep. 27, 1994

[54] SELECTIVE HERBIDICAL COMPOSITION COMPRISING OXETAN-3-OXYCARBONYLPHENYLSULFONYLUREA HERBICIDES AND QUINOLINE DERIVATIVES AS SAFENERS

[75] Inventors: Jutta Glock, Kaisten, Switzerland; Elmar Kerber, Görwihl, Fed. Rep. of Germany

[73] Assignee: Ciba-Geigy Corporation, Ardsley, N.Y.

[21] Appl. No.: 97,142

[22] Filed: Jul. 26, 1993

[30] Foreign Application Priority Data

Jul. 30, 1992 [CH] Switzerland ............... 2400/92-3
Aug. 26, 1992 [CH] Switzerland ............... 2647/92-4

[51] Int. Cl.⁵ .................... A01N 25/32; A01N 43/20
[52] U.S. Cl. ................................................ 504/105
[58] Field of Search .................................... 504/105

[56] References Cited

U.S. PATENT DOCUMENTS 4,902,340  2/1990  Hubele ................... 504/105
5,209,771  5/1993  Meyer .................... 504/178

FOREIGN PATENT DOCUMENTS 0094349  11/1983  European Pat. Off. .
0492366  7/1992   European Pat. Off. .
0492367  7/1992   European Pat. Off. .
0496701  7/1992   European Pat. Off. .

OTHER PUBLICATIONS

Chemical Abstracts, vol. 117, 126460c, (1992).
Chemical Abstracts, vol. 117, 150903v (1992).

Primary Examiner—Richard L. Raymond
Assistant Examiner—S. Mark Clardy
Attorney, Agent, or Firm—Edward McC. Roberts

[57] ABSTRACT

A selective herbicidal composition for controlling grasses and weeds in crops of useful plants comprises a) a herbicidally effective amount of a sulfonylurea of formula I

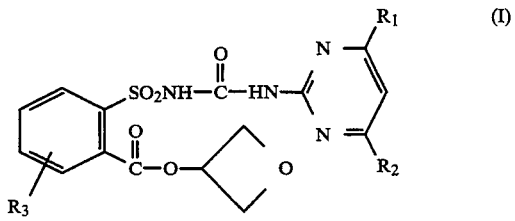

wherein
$R_1$ and $R_2$ independently of one another are methyl or methoxy;
$R_3$ is hydrogen, halogen, methyl or methoxy; and b) a herbicide-antagonistically effective amount of a quinoline derivative of formula II

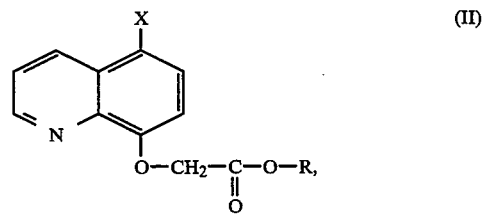

wherein
R is hydrogen or $C_1$–$C_8$ alkyl and
X is hydrogen or chlorine.

14 Claims, No Drawings

SELECTIVE HERBIDICAL COMPOSITION COMPRISING OXETAN-3-OXYCARBONYLPHENYLSULFONYLUREA HERBICIDES AND QUINOLINE DERIVATIVES AS SAFENERS

The present invention relates to a selective herbicidal composition for controlling grasses and weeds in crops of useful plants, especially in cereal crops, which comprises a herbicide and a safener (antidote) which protects the useful plants, but not the weeds, from the phytotoxic action of the herbicide, and to the use of that composition or of the combination of herbicide and safener in the control of weeds in crops of useful plants.

When herbicides are used, considerable damage may be caused to the crop planks depending on such factors as the concentration of herbicide and the mode of application, the species of crop plant, the nature of the soil and climatic conditions, for example period of exposure to light, temperature and rainfall. In particular, severe damage can be caused if, in the course of crop rotation, crop plants that are resistant to the herbicides are followed by other crop plants that have no or only insufficient resistance towards the herbicides.

In order to counter that problem, various compounds have already been proposed that are capable of specifically antagonizing the damaging effect of the herbicide on the crop plant, that is to say of protecting the crop plant without at the same time significantly affecting the herbicidal action against the weeds to be controlled. It has been found that the proposed safeners are often very species- or type-specific both as regards the crop planks and as regards the herbicide and in some cases also as a function of the mode of application, that is to say a specific safener is often suitable only for a specific crop plant and a specific class of herbicidal compound. For example, EP-A-0 094 349 discloses quinoline derivatives that protect crop plants from the phytotoxic action of herbicides of specific classes of compounds, such as phenoxypropionic acid ester herbicides, ureas, carbamates or diphenyl ethers.

It has now been found that very specific quinoline derivatives known from EP-A-0 094 349 are suitable for protecting crop plants front the phytotoxic action of a specific class of sulfonylurea herbicides.

There is therefore proposed according to the invention a selective herbicidal composition that, in addition to inert additives such as carriers, solvents and wetting agents, comprises as active component a mixture comprising a) a herbicidally effective amount of a sulfonylurea of formula I

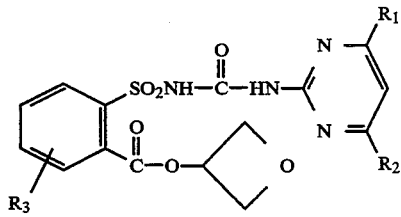

wherein
$R_1$ and $R_2$ independently of one another are methyl or methoxy; and
$R_3$ is hydrogen, halogen, methyl or methoxy; and b) as safener, a herbicide-antagonistically effective amount of a quinoline derivative of formula II

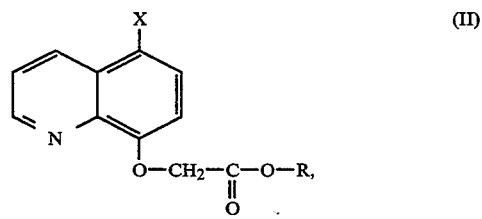

wherein
R is hydrogen or $C_1$-$C_8$ alkyl and
X is hydrogen or chlorine.

Suitable alkyl groups are straight-chained or branched alkyl groups, for example methyl, ethyl, n-propyl, isopropyl, n-butyl, isobutyl, sec-butyl or tert-butyl, and the various isomeric pentyl, hexyl, heptyl and octyl radicals.

Halogen is fluorine, chlorine, bromine or iodine, but preferably fluorine.

The compounds of formula I are capable of forming salts in which the hydrogen of the —$SO_2$—NH— group is replaced by a cation suitable for agriculture. Those salts are, for example, metal salts, especially alkali metal or alkaline earth metal salts, or ammonium salts or salts with organic amines.

Examples of amines suitable for the formation of ammonium cations are both ammonia and primary, secondary and tertiary $C_1$-$C_{18}$ alkylamines, $C_1$-$C_4$ hydroxyalkylamines and $C_2$-$C_4$ alkoxyalkylamines, for example methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methylethylamine, methyl-isopropylamine, methylhexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, such as pyridine, quinoline, isoquinoline, morpholine, piperidine, pyrrolidine, indoline, quinuclidine and azepine; primary arylamines, such as anilines, methoxyanilines, ethoxyanilines, o,m,p-toluidines, phenylenediamines, benzidines, naphthylamines and o,m,p-chloroanilines; but especially triethylamine, isopropylamine and diisopropylamine.

Compounds of formula I preferred for use in the composition according to the invention or the salts thereof are those wherein $R_3$ is hydrogen or 4-fluorine. Preference is also given to compounds of formula I wherein $R_1$ is methoxy. Suitable for those compounds are especially those safeners of formula II wherein X is chlorine and R is $C_4$-$C_8$ alkyl, especially 1-methylhexyl.

In very especially preferred compositions according to the invention a herbicidally effective sulfonylurea of formula I wherein $R_1$ is methyl and $R_2$ is methoxy is used. For those compositions according to the invention there are suitable especially those safeners of formula II wherein X is chlorine and R is $C_4$–$C_8$ alkyl, especially 1-methylhexyl.

A very especially preferred composition according to the invention comprises a herbicidally effective amount of a sulfonylurea of formula Ia

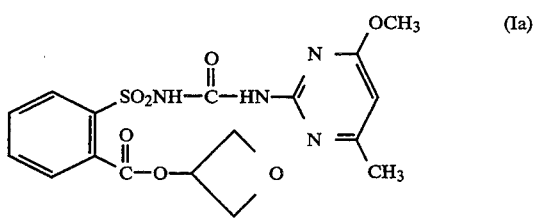

and as safener a herbicide-antagonistically effective amount of a quinoline derivative of formula IIa

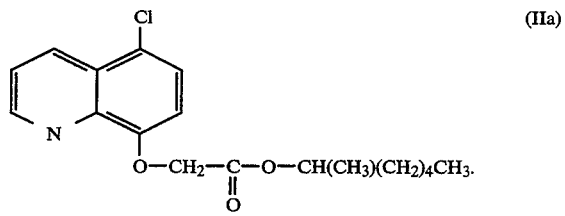

The sulfonylurea herbicides from the scope of formula I and the preparation thereof are known from EP-A-0 496 701.

The quinoline derivatives from the scope of formula II and the preparation thereof are likewise known and are described, for example, in patent specification EP-A-0 094 349.

The invention relates also to a method for the selective control of weeds in crops of useful plants, which method comprises treating the useful plants, the seeds or seedlings thereof or the cultivated area thereof with a herbicidally effective amount of the sulfonylurea of formula I and a herbicide-antagonistically effective amount of a quinoline derivative of formula II, simultaneously or independently of one another.

Crop plants that can be protected against the damaging effect of the above-mentioned herbicides by the quinoline derivatives of formula II are especially those that are important in the food and textile sectors, for example sugar cane and, especially, sorghum, maize, rice and other species of cereal, such as wheat, rye, barley and oats, preferably wheat, barley, rye and oats, but most especially wheat and barley.

The weeds to be controlled may be both monocotyledonous and dicotyledonous weeds.

There come into consideration as crop plants or parts of those plants, for example, those mentioned above. Cultivated areas will be understood as meaning areas of land in which the crop plants are already growing or in which the seed of those crop plants has already been sown, and also ground intended for growing those crop plants.

A safener or antidote of formula II can, depending on the intended use, be used to pre-treat the seed of the crop plant (dressing the seeds or seedlings) or can be introduced into the soil before or after sowing has taken place. It can, however, also be applied by itself or together with the herbicide before or after the emergence of the plants. The treatment of the plant or the seed with the safener can therefore in principle take place independently of the time of application of the phytotoxic chemical. The plant can, however, also be treated by applying the phytotoxic chemical and the safener simultaneously (tank mixture). Pre-emergence treatment includes both treatment of the cultivated area before sowing and treatment of cultivated areas in which seed has been sown but in which the plants have not yet grown.

The rate of application of the safener relative to that of the herbicide depends largely on the mode of application. In the case of field treatment, which is effected either using a tank mixture with a combination of safener and herbicide or by separate application of safener and herbicide, the ratio of safener to herbicide is generally from 1:100 to 10:1, preferably from 1:20 to 10:1.

In the case of field treatment, 0.001 to 5.0 kg of safener/ha, preferably 0.005 to 0.5 kg of safener/ha, will usually be applied.

The rate of application of herbicide is generally from 0.001 to 2 kg/ha, but preferably from 0.001 to 0.5 kg/ha.

In the case of seed-dressing, 0.001 to 10 g of safener/kg of seed, preferably 0.05 to 2 g of safener/kg of seed, will generally be applied. If the safener is applied in liquid form by seed soaking shortly before sowing, then it is advantageous to use safener solutions that comprise the active ingredient in a concentration of 1 to 10 000 ppm, preferably 100 to 1000 ppm.

For the purpose of application, the compounds of formula II or combinations of compounds of formula II with the herbicides to be antagonized are advantageously used together with the adjuvants conventionally employed in formulation technology, and are therefore formulated in known manner, e.g. into emulsifiable concentrates, coatable pastes, directly sprayable or dilutable solutions, dilute emulsions, wettable powders, soluble powders, dusts, granules, and also encapsulations in e.g. polymer substances. As with the nature of the compositions to be used, the methods of application, such as spraying, atomising, dusting, scattering, coating or pouring, are chosen in accordance with the intended objectives and the prevailing circumstances.

The formulations, i.e. the compositions, preparations or mixtures comprising the compound (active ingredient) of formula II, or a combination of the compound of formula II with the herbicide of formula I to be antagonized, and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are, for example, calcite or sand. In addition, a great number of pregranulated materials of inorganic or organic nature can be used, e.g. especially dolomite or pulverized plant residues.

Depending on the nature of the compound of formula II to be formulated and, where appropriate, also on the nature of the herbicide of formula I to be antagonized, suitable surface-active compounds are nonionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Fatty acid methyltaurin salts may also be mentioned.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$ alkyl radical which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 tool of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxy-polyethoxyethanol.

Fatty acid esters of polyoxyethylene sorbitan, e.g. polyoxyethylene sorbitan trioleate, are also suitable.

Cationic surfactants are preferably quaternary ammonium salts which contain, as N-substituent, at least one $C_8$–$C_{22}$ alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethyl-ammonium chloride or benzyldi(2-chloroethyl)ethylammonium bromide.

The surfactants customarily employed in formulation technology are described inter alia in the following publications: "Mc Cutcheon's Detergents and Emulsifiers Annual" MC Publishing Corp., Ridgewood, N.J., 1981. Stache, H., "Tensid-Taschenbuch", Carl Hanser Verlag, Munich/Vienna 1981.

The agrochemical compositions usually comprise 0.1 to 99 % by weight, preferably 0.1 to 95 % by weight, of a compound of formula II or a mixture of antidote and herbicide, 1 to 99.9 % by weight, preferably 5 to 99.8 % by weight, of a solid or liquid adjuvant and 0 to 25 % by weight, preferably 0.1 to 25 % by weight, of a surfactant.

Whereas commercial products are preferably formulated as concentrates, the end user will normally employ dilute formulations.

The compositions may also comprise further ingredients such as stabilizers, antifoams, viscosity regulators, binders and tackifiers, as well as fertilizers or other active ingredients for obtaining special effects.

Various methods and techniques are suitable for using compounds of formula II or compositions comprising them for protecting crop plants against the damaging effects of herbicides of formula I. The following are examples thereof:

i) Seed dressing a) dressing the seeds with a wettable powder formulation of a compound of formula II by shaking in a vessel until the formulation is evenly distributed over the surface of the seeds (dry dressing). Approximately 1 to 500 g of a compound of formula II (4 g to 2 kg of wettable powder) are used per 100 kg of seed.

b) dressing the seeds with an emulsifiable concentrate of a compound of formula II according to method a) (wet dressing).

c) dressing by immersing the seeds in a mixture comprising 100 to 1000 ppm of a compound of formula II for 1 to 72 hours and, if desired, subsequently drying the seeds (seed soaking).

Normally 1 to 1000 g of antidote, preferably 5 to 250 g of antidote, are used per 100 kg of seed, although, depending on the method employed, which also allows the addition of other active ingredients or micronutrients, amounts that exceed or fall short of the specified concentration limits may be employed (repeat dressing).

ii) Application from a tank mixture

A liquid formulation of a mixture of antidote and herbicide (ratio of the one to the other from 10:1 to 1:100) is used, the rate of application of herbicide being 0.001 to 2.0 kg per hectare. A tank mixture of this type is applied before or after sowing.

iii) Application to the seed furrow

The antidote is introduced in the form of an emulsifiable concentrate, wettable powder or granules into the open, sown seed furrow and then, after covering the seed furrow, the herbicide is applied preemergence in the normal manner.

iv) Controlled release of active ingredient

A solution of a compound of formula II is applied to mineral granule carriers or polymerised granules (urea/formaldehyde) and allowed to dry. If desired, a coating may be applied (coated granules) that allows the active ingredient to be released in metered amounts over a specific period of time.

FORMULATION EXAMPLES FOR MIXTURES OF FORMULA I WITH THE SAFENER OF FORMULA II (THROUGHOUT, PERCENTAGES ARE BY WEIGHT)

| F1. Solutions | a) | b) | c) | d) |
| --- | --- | --- | --- | --- |
| compound mixture | 5% | 10% | 50% | 90% |
| dipropylene glycol methyl ether | — | 20% | 20% | — |
| polyethylene glycol (mol. wt. 400) | 20% | 10% | — | — |
| N-methyl-2-pyrrolidone | — | — | 30% | 10% |
| aromat. hydrocarbon mixture $C_9$-$C_{12}$ | 75% | 60% | — | — |

These solutions are suitable for application in the form of micro-drops.

| F2. Wettable powders | a) | b) | c) | d) |
| --- | --- | --- | --- | --- |
| compound mixture | 5% | 25% | 50% | 80% |
| sodium lignosulfonate | 4% | — | 3% | — |
| sodium laurylsulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is thoroughly mixed with the adjuvants and the mixture is thoroughly ground in a suitable mill, affording wettable powders which can be diluted with water to give suspensions of the desired concentration.

| F3. Coated granules | a) | b) | c) |
| --- | --- | --- | --- |
| compound mixture | 0.1% | 5% | 15% |
| highly dispersed silicic acid | 0.9% | 2% | 2% |
| inorganic carrier (diameter 0.1-1 mm) such as $CaCO_3$ or $SiO_2$ | 99.0% | 93% | 83% |

The active ingredient is dissolved in methylene chloride and sprayed onto the carrier, and the solvent is then evaporated off in vacuo.

| F4. Coated granules | a) | b) | c) |
| --- | --- | --- | --- |
| compound mixture | 0.1% | 5% | 15% |
| polyethylene glycol (mol. wt. 200) | 1.0% | 2% | 3% |
| highly dispersed silicic acid | 0.9% | 1% | 2% |
| inorganic carrier (diameter 0.1-1 mm) such as $CaCO_3$ or $SiO_2$ | 98.0% | 92% | 80% |

The finely ground active ingredient is uniformly applied, in a mixer, to the carrier moistened with the polyethylene glycol. Non-dusty coated granules are obtained in this manner.

| F5. Extruder granules | a) | b) | c) | d) |
| --- | --- | --- | --- | --- |
| compound mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F6. Dusts | a) | b) | c) |
| --- | --- | --- | --- |
| compound mixture | 0.1% | 1% | 5% |
| talcum | 39.9% | 49% | 35% |
| kaolin | 60.0% | 50% | 60% |

Ready-for-use dusts are obtained by mixing the active ingredient with the carriers and grinding the mixture in a suitable mill.

| F7. Suspension concentrates | a) | b) | c) | d) |
| --- | --- | --- | --- | --- |
| compound mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

BIOLOGICAL EXAMPLES

The ability of the compounds of formula II to protect crop plants from the phytotoxic action of strong herbicides is shown by the following Examples.

EXAMPLE B1: POST-EMERGENCE PHYTOTOXIC ACTION OF THE HERBICIDES OF FORMULA I AND OF THE MIXTURES OF HERBICIDE WITH SAFENER OF FORMULA II ON WHEAT AND BARLEY

Under greenhouse conditions, wheat and barley are grown in plastics pots to the 4-leaf stage. At that stage, the herbicide of Table 1 by itself and the mixtures of the herbicide with the safeners of Table 2 are applied to the test plants. The test compounds are applied in the form of an aqueous suspension according to Example F7 in 500 1 of water/ha, 28 days after application the test is evaluated according to a scale of percentages. 100% denotes that the test plant has died, 0 % denotes no phytotoxic action. The results shown in Table B1 are obtained. The results show that using the safeners of Table 2 the damage to wheat and barley caused by the herbicide of Table 1 can be clearly reduced.

TABLE 1

Compounds of formula I:

TABLE 1-continued

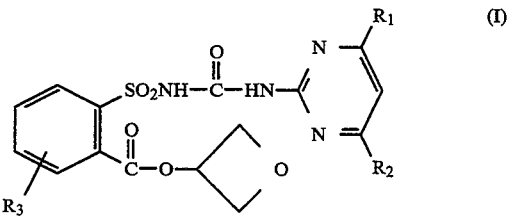

| Comp. No. | R₁ | R₂ | R₃ | phys. data |
|---|---|---|---|---|
| 1.01 | CH₃ | CH₃ | H | |
| 1.02 | OCH₃ | CH₃ | H | |
| 1.03 | OCH₃ | OCH₃ | H | |
| 1.04 | CH₃ | OCH₃ | 4-F | decomp. >140° C. |

TABLE 2

Compounds of formula II:

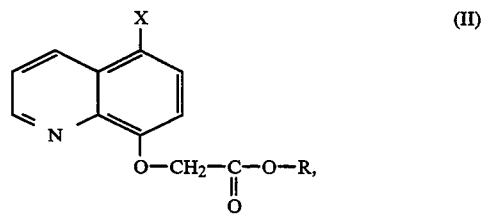

| Comp. No. | X | R |
|---|---|---|
| 2.01 | Cl | 1-methylhexyl |
| 2.02 | Cl | hydrogen |
| 2.03 | Cl | n-octyl |
| 2.04 | Cl | 1-methylpropyl |

TABLE B1

The rate of application of the safener in the following Table is 125 g of a.i./ha.

| Herbicide Comp. No. | Rate of application of herbicide | Safener Comp. No. | Phytotoxic action in % wheat | barley |
|---|---|---|---|---|
| 1.01 | 60 g/ha | — | — | 80 |
| 1.01 | 30 g/ha | — | — | 65 |
| 1.01 | 60 g/ha | 2.01 | — | 40 |
| 1.01 | 30 g/ha | 2.01 | — | 20 |
| 1.02 | 15 g/ha | — | 85 | — |
| 1.02 | 15 g/ha | 2.01 | 15 | — |
| 1.02 | 15 g/ha | 2.02 | 15 | — |
| 1.02 | 15 g/ha | 2.03 | 25 | — |
| 1.02 | 15 g/ha | 2.04 | 15 | — |
| 1.03 | 15 g/ha | — | — | 70 |
| 1.03 | 8 g/ha | — | — | 40 |
| 1.03 | 15 g/ha | 2.01 | — | 30 |
| 1.03 | 8 g/ha | 2.01 | — | 10 |
| 1.04 | 60 g/ha | — | 15 | 40 |
| 1.04 | 60 g/ha | 2.01 | 0 | 20 |

The same results are obtained when the compounds of formulae I and II are formulated in accordance with Examples F1 to F6.

What is claimed is:

1. A composition for the selective control of weeds in crops of useful plants, which, in addition to inert carriers and additives, comprises as active ingredient a mixture comprising
a) a herbicidally effective amount of a sulfonylurea of formula I

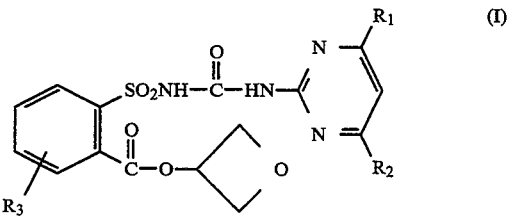

wherein
$R_1$ and $R_2$ independently of one another are methyl or methoxy;
$R_3$ is hydrogen, halogen, methyl or methoxy; and
b) as safener, a herbicide-antagonistically effective amount of a quinoline derivative of formula II

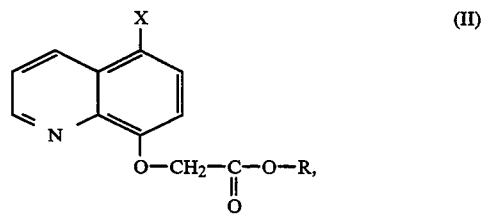

wherein
R is hydrogen or $C_1$-$C_8$ alkyl and
X is hydrogen or chlorine.

2. A composition according to claim 1 wherein $R_3$ is hydrogen.

3. A composition according to claim 1 wherein $R_3$ is 4-fluorine.

4. A composition according to claim 1 wherein $R_1$ is methoxy.

5. A composition according to claim 4 wherein X is chlorine and R is $C_4$-$C_8$ alkyl.

6. A composition according to claim 5 wherein R is 1-methylhexyl.

7. A composition according to claim 1 wherein $R_1$ is methyl and $R_2$ is methoxy.

8. A composition according to claim 7 wherein X is chlorine and R is $C_4$-$C_8$ alkyl.

9. A composition according to claim 8 wherein R is 1-methylhexyl.

10. A composition according to claim 1 comprising a herbicidally effective amount of a sulfonylurea of formula Ia

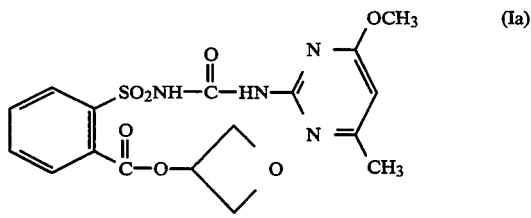

and, as safener, a herbicide-antagonistically effective amount of a quinoline derivative of formula IIa

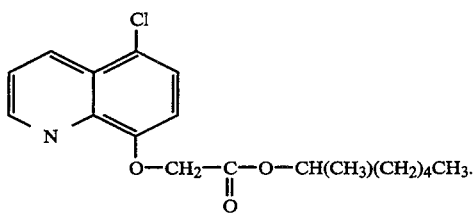
(IIa)

11. A method for the selective control of weeds and grasses in crops of useful plants, which comprises treating the crops, the seeds thereof or the cultivated area thereof with an effective amount of a herbicide of formula I according to claim 1 and a herbicide-antagonistically effective amount of a compound of formula II according to claim 1, simultaneously or independently of one another.

12. A method according to claim 11, which comprises treating crop plants or cultivated areas intended for crop plants with 0.001 to 2 kg/ha of a compound of formula I and an amount of 0.001 to 5 kg/ha of a compound of formula II.

13. A method according to claim 11 for the selective control of weeds and grasses in cereal crops.

14. A method according to claim 13, wherein the cereal crops are wheat or barley.

* * * * *